(12) United States Patent
Simon et al.

(10) Patent No.: US 9,097,384 B1
(45) Date of Patent: Aug. 4, 2015

(54) SUPPORT APPARATUS FOR RADIOTHERAPY MEASUREMENT SYSTEM

(71) Applicant: Sun Nuclear Corporation, Melbourne, FL (US)

(72) Inventors: Thomas A. Simon, Rockledge, FL (US); Mark Rose, Cocoa, FL (US); Jeffrey P. Zack, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 126 days.

(21) Appl. No.: 13/691,663

(22) Filed: Nov. 30, 2012

Related U.S. Application Data

(60) Provisional application No. 61/565,334, filed on Nov. 30, 2011.

(51) Int. Cl.
   *B62B 3/00* (2006.01)
   *B62B 1/00* (2006.01)
   (Continued)

(52) U.S. Cl.
   CPC .............. *F16M 11/20* (2013.01); *F16M 11/24* (2013.01); *F16M 11/42* (2013.01)

(58) Field of Classification Search
   CPC ....... F16M 11/00; F16M 11/42; F16M 11/04; F16M 11/28; F16M 11/32; F16M 11/34; F16M 11/24; F16M 11/20; F16M 11/242; A47B 9/00; A47B 9/18; A47B 9/10; A61B 6/00; A61B 6/04; A61B 6/4405; B62B 1/264; B62B 1/26; B62B 2202/02; B62B 2301/08; B62B 2301/04; B62B 2301/044; B62B 1/12; B62B 1/14; B62B 1/18; B62B 1/20; B62B 3/00; B62B 3/002; B62B 3/02; B62B 3/008; B62B 3/0606; B62B 3/0618; B62B 3/0643

USPC ............. 280/1, 29, 651, 47.34, 47.33, 43, 30, 280/43.15, 43.16, 43.17, 47.41, 47.21, 62, 280/64, 79.11, 79.2, 79.6, 79.7, 47.17, 280/47.16, 47.18; 378/204; 254/2 B, 133 R, 254/134, 93 R, 129, 145.6, 161, 188.5; 606/1–8, 130, 33; 108/144.11, 147
   See application file for complete search history.

(56) References Cited

U.S. PATENT DOCUMENTS 1,239,145 A * 9/1917 Wantz ........................... 378/197
2,818,510 A * 12/1957 Verse ............................ 378/189
(Continued)

FOREIGN PATENT DOCUMENTS

EP            1060726 A1     12/2000
JP            05-154209       6/1993

OTHER PUBLICATIONS

International Search Report issued in International Application No. PCT/US2012/053440 mailed Mar. 26, 2013.
(Continued)

*Primary Examiner* — J. Allen Shriver, II
*Assistant Examiner* — James M Dolak
(74) *Attorney, Agent, or Firm* — Mintz Levin Cohn Ferris Glovsky and Popeo, P.C.

(57) ABSTRACT

A lift table provides stability and portability for a radiation measurement scanning system. The lift table may be fixed for radiation measurement or configured for storage. Further, the lift table may be easily disassembled and assembled to allow efficient transporting. The lift table supports a multiple axes scanning system for measuring radiation from a radiation source, such as a linear accelerator (LINAC) and includes a leveling platform, all of which are provided by a desirable weight and portability.

24 Claims, 5 Drawing Sheets

(51) Int. Cl.
  *F16M 11/20* (2006.01)
  *F16M 11/24* (2006.01)
  *F16M 11/42* (2006.01)

(56) References Cited

U.S. PATENT DOCUMENTS

| | | | |
|---|---|---|---|
| 3,783,251 A | 1/1974 | Pavkovich | |
| 4,887,287 A * | 12/1989 | Cobben | 378/198 |
| 5,099,505 A | 3/1992 | Seppi et al. | |
| 5,160,337 A | 11/1992 | Cosman | |
| 5,388,142 A * | 2/1995 | Morris | 378/198 |
| 5,627,367 A | 5/1997 | Sofield | |
| 5,712,482 A * | 1/1998 | Gaiser et al. | 250/363.08 |
| 6,131,690 A * | 10/2000 | Galando et al. | 180/411 |
| 6,257,552 B1 * | 7/2001 | Crow et al. | 254/2 B |
| 6,261,219 B1 | 7/2001 | Meloul et al. | |
| 6,535,756 B1 | 3/2003 | Simon et al. | |
| 6,609,826 B1 * | 8/2003 | Fujii et al. | 378/198 |
| 6,799,068 B1 | 9/2004 | Hartmann et al. | |
| 6,990,368 B2 | 1/2006 | Simon et al. | |
| 7,016,454 B2 * | 3/2006 | Warnberg | 378/9 |
| 7,065,812 B2 * | 6/2006 | Newkirk et al. | 5/600 |
| 7,453,976 B1 | 11/2008 | Yin | |
| 7,579,608 B2 | 8/2009 | Takahashi et al. | |
| 7,945,022 B2 | 5/2011 | Nelms et al. | |
| 8,044,359 B2 | 10/2011 | Simon | |
| 8,136,773 B2 * | 3/2012 | Schmutzer et al. | 248/125.8 |
| 8,218,718 B1 | 7/2012 | Van Herk et al. | |
| 8,235,530 B2 | 8/2012 | Maad | |
| 8,242,458 B2 | 8/2012 | Rinecker et al. | |
| 8,321,179 B2 | 11/2012 | Simon et al. | |
| 8,430,564 B2 * | 4/2013 | Simmons et al. | 378/198 |
| 8,457,713 B2 * | 6/2013 | Kagermeier | 600/411 |
| 8,474,794 B2 * | 7/2013 | Liljedahl | 254/120 |
| 8,536,547 B2 | 9/2013 | Maurer, Jr. et al. | |
| 8,541,756 B1 | 9/2013 | Treas | |
| 8,726,814 B1 * | 5/2014 | Matteo | 108/50.02 |
| 8,794,899 B2 * | 8/2014 | Cozza et al. | 414/458 |
| 8,833,709 B2 * | 9/2014 | Weng | 248/129 |
| 8,840,304 B2 * | 9/2014 | Perez Zarate et al. | 378/198 |
| 8,874,385 B2 | 10/2014 | Takayanagi et al. | |
| 2006/0203967 A1 | 9/2006 | Nilsson | |
| 2007/0041499 A1 | 2/2007 | Lu et al. | |
| 2007/0086577 A1 | 4/2007 | Kobayashi | |
| 2008/0118137 A1 | 5/2008 | Chen et al. | |
| 2011/0022360 A1 | 1/2011 | Simon et al. | |
| 2011/0096906 A1 | 4/2011 | Langeveld | |
| 2011/0248188 A1 | 10/2011 | Brusasco et al. | |
| 2011/0306864 A1 * | 12/2011 | Zarate et al. | 600/407 |
| 2012/0014618 A1 | 1/2012 | Sun et al. | |
| 2012/0025105 A1 | 2/2012 | Brown et al. | |
| 2012/0326057 A1 | 12/2012 | Remeijer et al. | |
| 2013/0048883 A1 | 2/2013 | Simon et al. | |
| 2014/0073834 A1 | 3/2014 | Hildreth et al. | |
| 2014/0263990 A1 | 9/2014 | Kawrykow et al. | |

OTHER PUBLICATIONS

International Search Report Issued in International Application No. PCT/US2014/065808 mailed Feb. 17, 2015.

* cited by examiner

SUPPORT APPARATUS FOR RADIOTHERAPY MEASUREMENT SYSTEM

CROSS-REFERENCE TO RELATED APPLICATION

This application claims the benefit of U.S. Provisional Patent Application Ser. No. 61/565,334, filed on Nov. 30, 2011, the contents of which are herein incorporated by reference in their entirety.

FIELD OF THE INVENTION

The invention generally relates to radiation therapy and in particular to systems and methods for measuring a dose in a phantom for commissioning treatment planning systems in radiation therapy beam delivery.

BACKGROUND OF THE INVENTION

Commissioning a linear accelerator (LINAC) for clinical use typically requires a water tank dosimetry scanner. By way of example, for commissioning a treatment planning system (TPS) for clinical use, medical physicists are faced with a need for precision during set up of measuring equipment and testing. Since commissioning beam data is treated as a reference and ultimately used by the TPS, it is vitally important that collected (i.e., scanned) data be of the highest quality to avoid dosimetric and patient treatment errors that may subsequently lead to a poor treatment outcome. It is therefore important that the scanner being used, regardless of style, must be stable under typical use conditions. In particular, and by way of example, a table used to support the scanner should be able to support the weight of a tank filled with water while maintaining stability. There needs to be stability while personnel work around the table supporting the scanner, especially when there are portions of the floor that are typically unstable, such as the bearing floor portion used to rotate the couch. The table should be able to maintain its stability during weight load changes as water is added and removed from the tank during, by way of example, tissue phantom ratio (TPR) measurements.

In addition to stability during measurement procedures, there remains a need for stability and portability during transport of the tank at a facility and storage at that or related facility. Also, there remains a need for stability and portability such that the scanner will not be damaged or unacceptably misaligned during transport between facilities.

As described in U.S. Pat. No. 8,321,179 for Multiple Axes Scanning System and Method for Measuring Radiation from a Radiation Source, the contents of which are hereby incorporated by reference in their entirety, there is a need for an accurate scan measurement of relative dose in a water phantom.

The measurement session of the LINAC beam scanning can take many days. During these long scanning times, there are no assurances from the radiation measurement scanning system to indicate that the scanning system or the LINAC has not changed during scans in a way that would affect the measurement data. It is incumbent upon the operator to perform periodic quality assurance (QA) tests that would reveal such changes in the scanner system. The measurement session of the LINAC beam scanning will typically include many setups. During these many setups, it is important to know that the measuring equipment has been properly and reproducibly installed. The stability or lack thereof provided by the table is clearly important.

The use of a LINAC for external beam irradiation and radiotherapy is well known. As presented in U.S. Pat. No. 5,160,337 to Cosman (the contents of which are also herein incorporated by reference in their entirety), a LINAC delivers a beam of photons or electrons through a collimated slit system and has multiple degrees of freedom, wherein a gantry rotates about a horizontal axis that is defined by a gantry bearing anchored to a housing which is anchored to the floor. The gantry can swing in an arc. The photon beam emerges from a collimator and aims at a target. A couch is connected to a rotating floor bearing, and both the floor bearing and the couch rotate about a vertical axis. In use, a patient lies on top of the movable couch, which can move in multiple directions to locate an anatomical target at the intersection of two axes, referred to as the isocenter of the LINAC. The couch sweeps around the vertical axis along an arc in a horizontal plane.

The couch is attached via the floor bearing and rotates about the vertical axis. In the event that the floor or couch bearing is unstable, stability can be achieved by an independent, collision-free or curved-shaped floor stand by anchoring a bearing mount to the floor. The fact that the bearing is independent of the couch bearing can result in aberrations in the stability of the floor bearing relative to the vertical axis.

There is a need for a support for radiation measuring systems that can accommodate various LINAC setups and be sufficiently portable to allow a user to efficiently and effectively move radiation measuring equipment into place with an assurance of accuracy and repeatability.

SUMMARY OF THE INVENTION

In view of the foregoing, it is an object of the present invention to provide an improved support apparatus for a radiotherapy measurement system. According to an embodiment of the present invention, the support apparatus includes a table base assembly and a frame assembly. The table base assembly has an upper base end and a lower base end, the upper base end being adapted to support a leveling assembly for the radiotherapy measurement system. The lower base end is mounted to the frame assembly, which has a plurality of frame assembly legs movable to increase and decrease an effective footprint of the frame assembly.

According to an aspect of the present invention, the frame assembly has a central frame portion, a plurality of frame assembly legs and plurality of casters. The lower base end is mounted to the center frame portion, which includes a pair of generally opposed first sides connected by a pair of generally opposed second sides. The legs are arranged in first and second pairs of frame assembly legs. Each of the frame assembly legs includes a proximal end and distal end, and each proximal end is pivotably connected to a respective end of one of the first sides such that the first and second pairs of frame assembly legs are pivotable from a closed position, in which their respective distal ends are adjacent to their respective first side and to each other, to a measurement position, in which their respective distal ends are spaced outwardly from their respective first side and apart from each other. The casters each extend downwardly from one of the distal ends.

According to a further aspect, the first and second pairs of frame assembly legs are further pivotable to a travel position, in which an overall length of the frame assembly is increased and an overall width of the frame assembly is decreased relative to the measurement position.

These and other objects, aspects and advantages of the present invention will be better appreciated in view of the drawings and following detailed description of preferred embodiments.

DETAILED DESCRIPTION OF PREFERRED EMBODIMENTS

Figure 1:
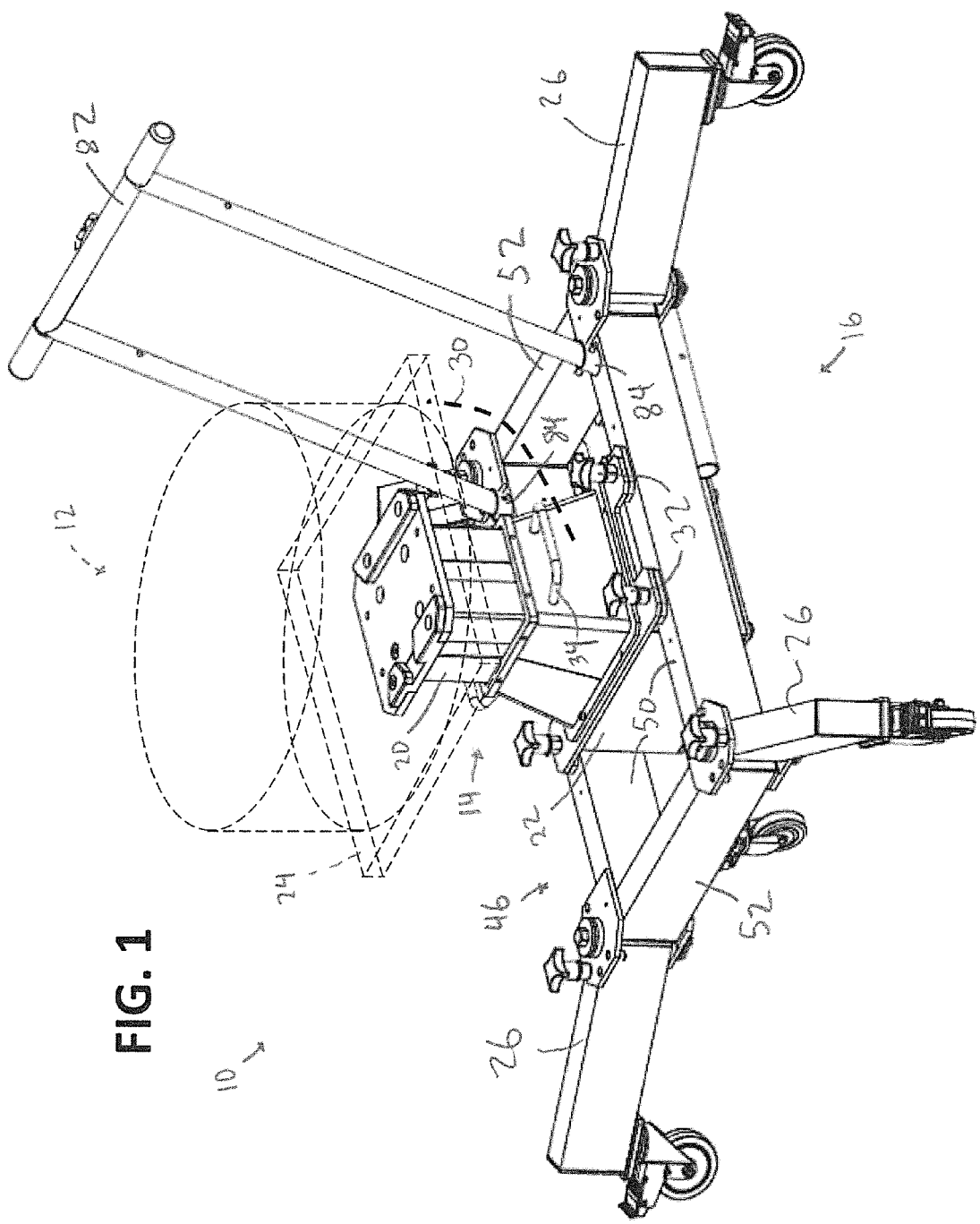
FIG. 1 is a perspective view of a support apparatus for a radiotherapy measurement system, including a table base assembly and a frame assembly, according to an embodiment of the present invention.
Figure 2:
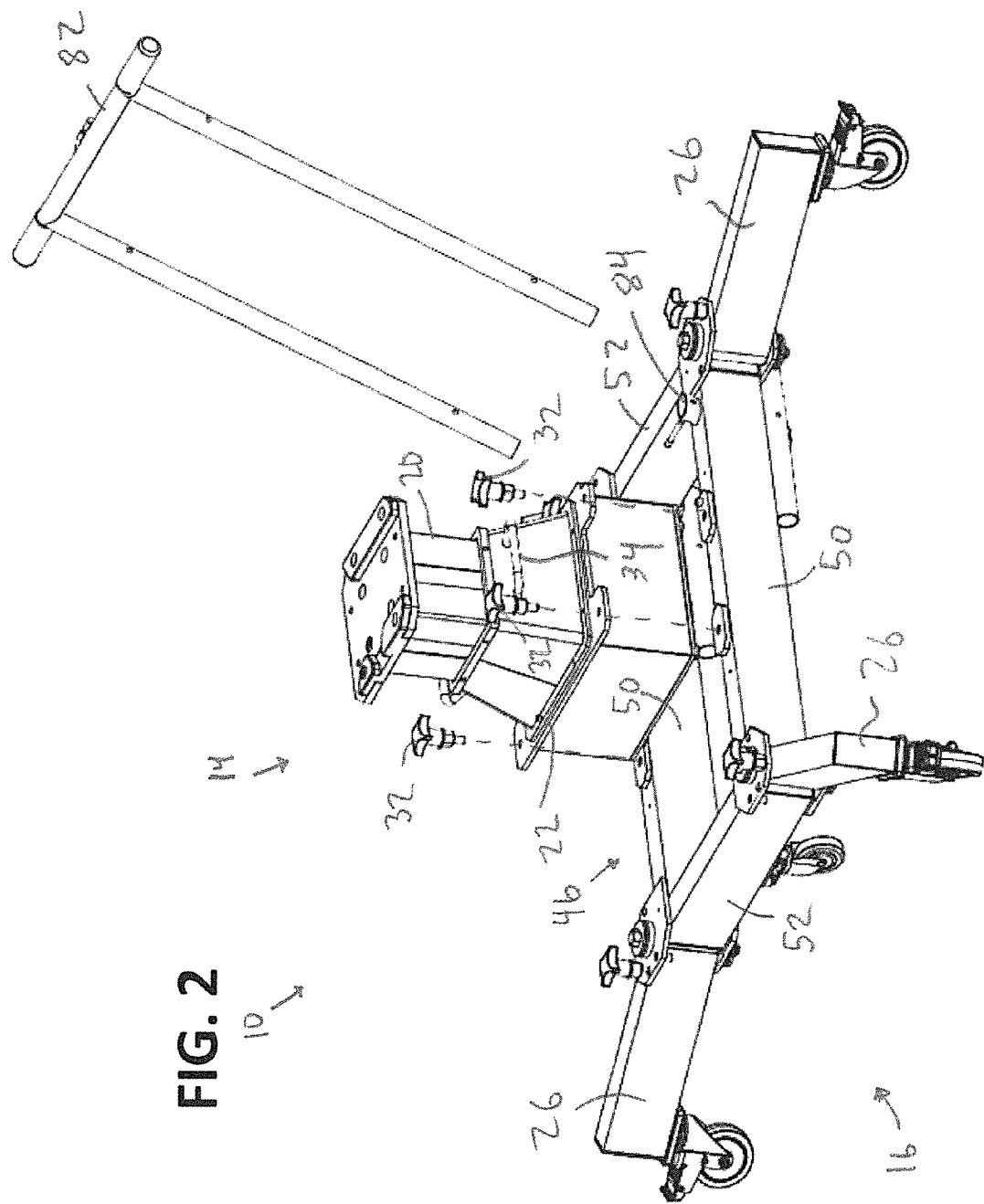
FIG. 2 is a partially exploded perspective view of the support apparatus of FIG. 1.

Referring to FIGS. 1 and 2, according to an embodiment of the present invention, a support apparatus 10 for a radiotherapy measurement system 12 includes a table base assembly 14 and a frame assembly 16. The table base assembly 14 has an upper base end 20 and a lower base end 22. The upper base end 20 is adapted to support the radiotherapy measurement system 12 via a leveling assembly 24 and the lower base end 22 connects to the frame assembly 16. The frame assembly 16 has a plurality of frame assembly legs 26, which are movable to increase and decrease an effective footprint of the frame assembly 16.

The table base assembly 14 incorporates a vertical actuator, with the top end 20 forming a piston received by the bottom end 22 that can raise and lower relative thereto. Power and command signals are transmitted to the table base assembly 14 for operation of the vertical actuator via a cable 30 from the leveling assembly 24.

The table base assembly 14 is removably connected to the frame assembly 16 by a plurality of locking knobs 32. Preferably, the locking knobs 32 thread into the frame assembly 16, although other connection mechanisms could be employed. To facilitate installation and removal of the table assembly 14, one or more base handles 34 are arranged on sides of the bottom end 22.

Figure 3:
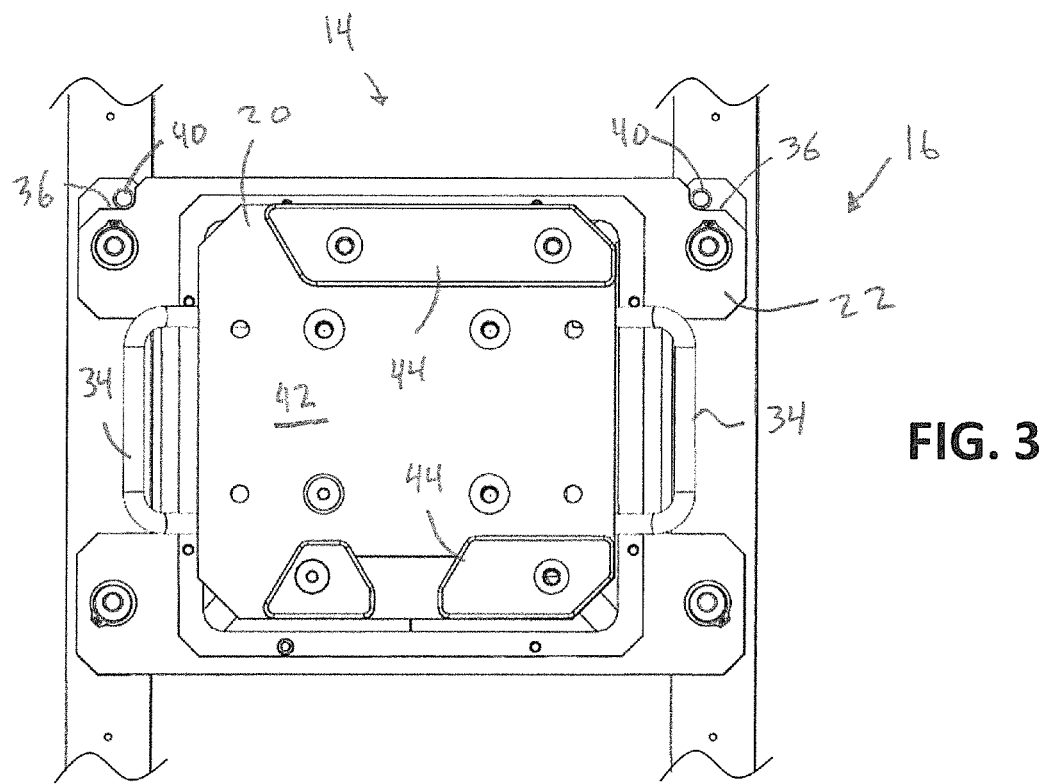
FIG. 3 is a detail top view of the table base assembly of FIG. 1 at its interface with the frame assembly.

Referring to FIG. 3, to ensure proper alignment of the table base assembly 14 on the frame assembly 16, complementary keyed portions 36, 40 are formed on each. Similarly, to ensure proper alignment of the leveling assembly 24, a top plate 42 with keyed portions 44 is arranged on the upper end 20. Additionally, adjustments can be made to the bottom end 22 to adjust the level of the table base assembly 14 relative to the frame assembly 16.

Referring again to FIGS. 1 and 2, the frame assembly 16 advantageously includes a center frame portion 46 to which the plurality of frame assembly legs 26 are attached. Preferably, the center frame portion has opposed pairs of first and second sides 50, 52, with the arms 26 being pivotably connected in pairs at the intersections therebetween, such that the pivoting of the arms 26 relative to the center frame portion 46 effects the expansion and contraction of the effective footprint of the frame assembly 16.

Figure 4:
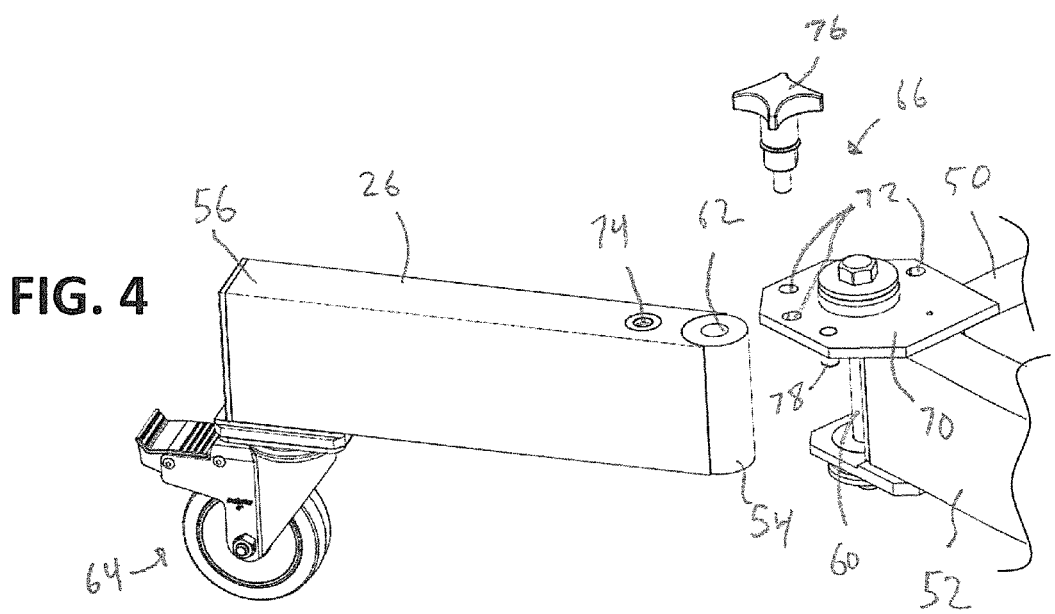
FIG. 4 is a partially exploded perspective view of a representative leg of the frame assembly of FIG. 1.

Referring to FIG. 4, an exemplary one of the frame assembly legs 26 is shown. The other frame assembly legs 26 substantially resemble the frame assembly leg of FIG. 4, with the orientation of connections to the center frame portion 46 being altered depending on the position of the legs 26. Each leg 26 has a proximal end 54 and a distal end 56. The proximal end 54 pivotably attaches at the corresponding intersection of the first and second sides 50, 52, preferably using a pivot pin 60 inserted through a corresponding bore 62.

The distal end 56 of each frame assembly leg 26 has a caster 64 extending downwardly therefrom. Preferably, each caster 64 is selectively lockable, both with respect to its rolling and rotating motion, to help fix the position of the support assembly 10 once in position, and also to facilitate transport in a straight line by not allowing all of the casters 64 to rotate at the same time.

Advantageously, there is also a locking mechanism 66 associated with each of the frame assembly legs 26 to releasably lock them in one of a plurality of predetermined positions. The locking mechanism 26 includes a flange 70 with a plurality of holes 72 that align with a locking hole 74 in the arm 26 when the arm 26 is in one of the predetermined positions. A locking pin 76 is inserted through the corresponding one of the holes 72 into the locking hole 74 to releasable fix the position. The locking pin 76 can thread into the locking hole 74 for more secure retention. Additionally, other locking mechanisms for some or all of the predetermined positions could be employed. A limiting peg 78 is provided to limit the pivoting motion of the leg 26.

Figure 5:
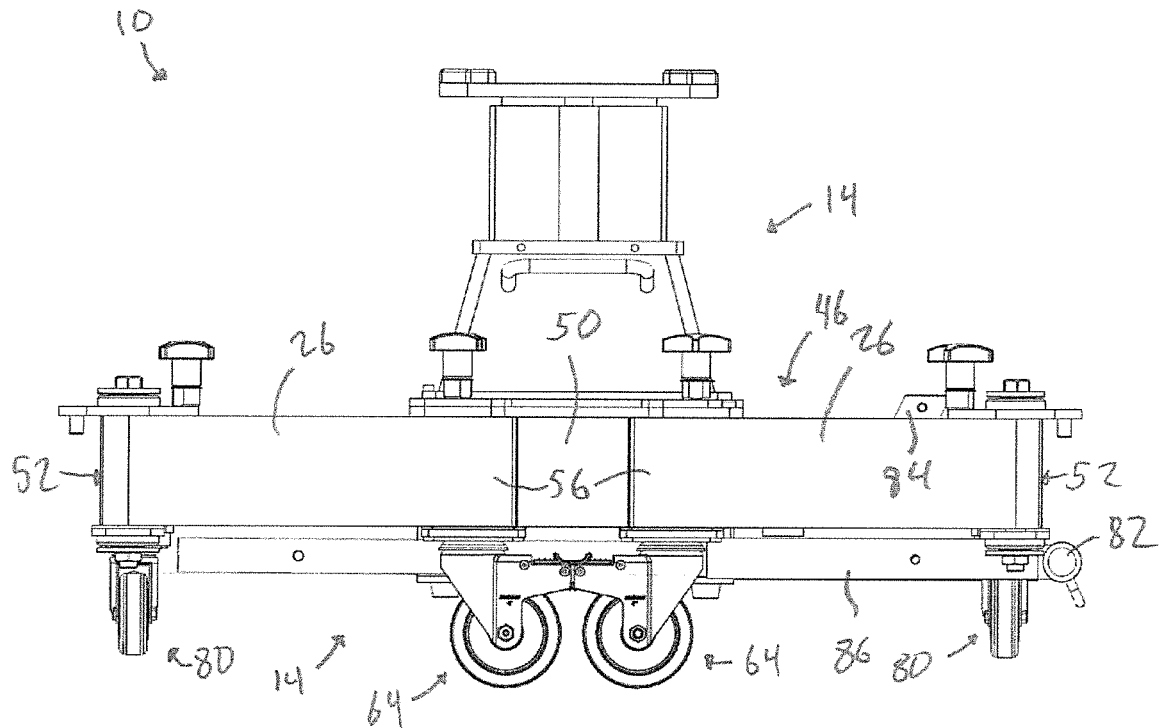
FIG. 5 is a side view of the support apparatus of FIG. 1, in a closed configuration.

In FIGS. 1 and 2, the legs 26 are depicted locked into a measurement position, which corresponds to an expanded effective footprint in which the overall length and width of the frame assembly 16 are both increased. In FIG. 5, opposite pairs of the legs 26 are pivoted against the first sides 50, such that the overall width and length of the frame assembly 10 are at a minimum. In this closed position, the distal ends 56 of each pair of legs 26 are adjacent to each other and to their respective first side 50.

In the closed position, the casters 64 are very close to one another, making it easier for the support assembly 10 to tip towards the second sides 52. To compensate during any tipping, casters 80 extend downwardly from midpoints of the second sides 52. Casters 80 preferably do not extend downwardly as far as casters 64, such that they can only contact the floor under the support assembly 10 when in the closed position. The casters 80 and tipping tendency of the support assembly 10 can advantageously assist when trying to move the support assembly 10 over an uneven threshold.

Referring again to FIGS. 1 and 2, to facilitate movement of the support assembly 82, a handle 82 attaches to the frame assembly 16. Preferably, the handle 82 is releasably attached in angled mounting tubes 84 so as to extend upwardly and rearwardly from the frame center portion 46. Referring to FIG. 5, for more compact storage, the handle 82 can be removed from the tubes 84 and releasably connected under the center frame portion 46 in a horizontal orientation using storage tubes 86.

Figure 6:
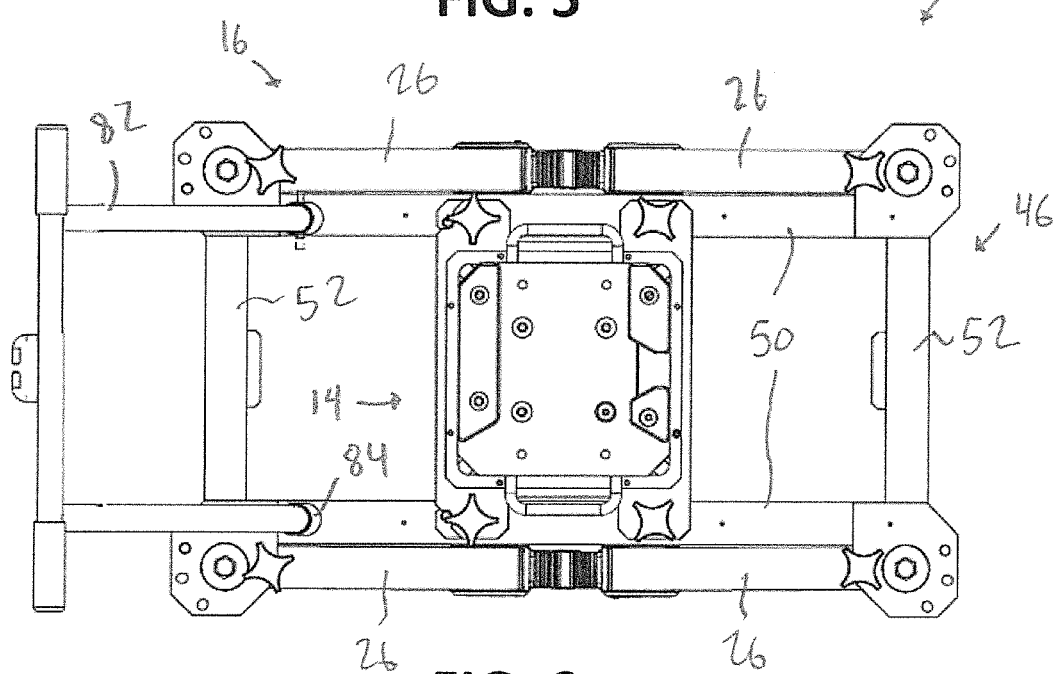
FIG. 6 is a top view of the support apparatus of FIG. 1, in the closed configuration.

Exemplary operations of the support assembly 10 will be described with reference to FIGS. 5-8. In FIG. 5, the support assembly 10 is in its most compact configuration, with the legs 46 locked in the closed position and the handle 82 secured below the center frame portion 46. In FIG. 6, the handle 82 is secured in its generally upright position in the angled mounting tubes 84. If desired, the support assembly 10 could be transported short distances in this configuration, although with the leveling assembly 24 and radiotherapy measurement system 12 mounted thereon, this could prove unwieldy.

Figure 7:
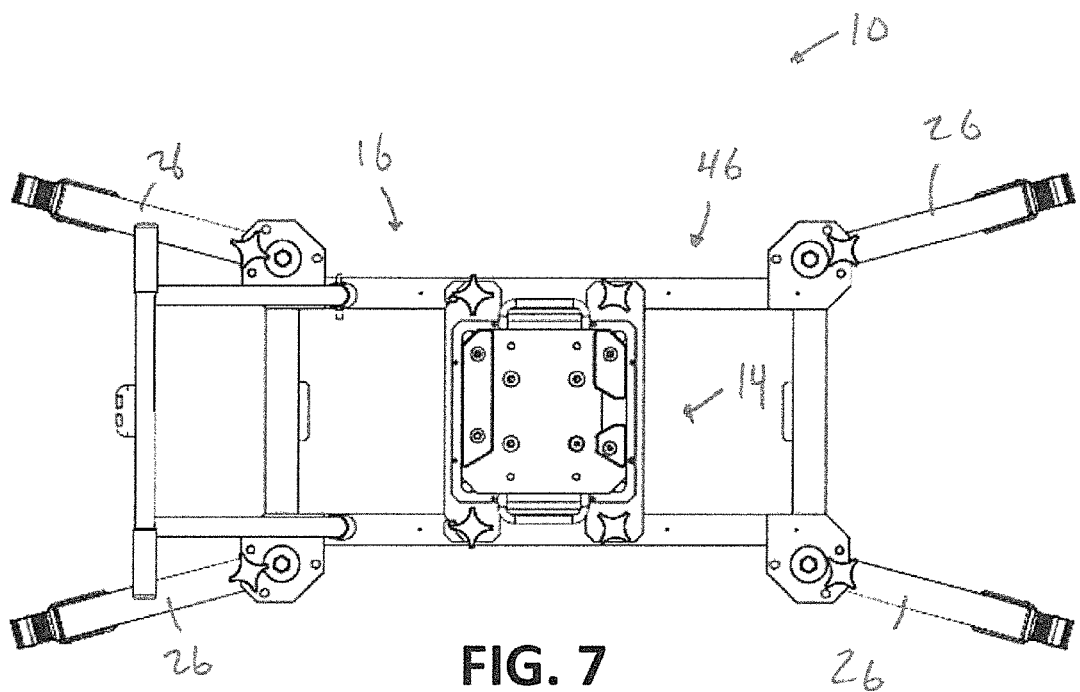
FIG. 7 is a top view of the support apparatus of FIG. 1, in a travel configuration.

Preferably, as depicted in FIG. 7, both pairs of legs 26 are moved and locked into a travel position. In the travel position, the overall width of the frame assembly 16 is reduced relative to the measurement position (see FIG. 8), but the overall length is increased. Thus the support assembly 10 can be more readily pushed in straight lines and navigated through doors.

Figure 8:
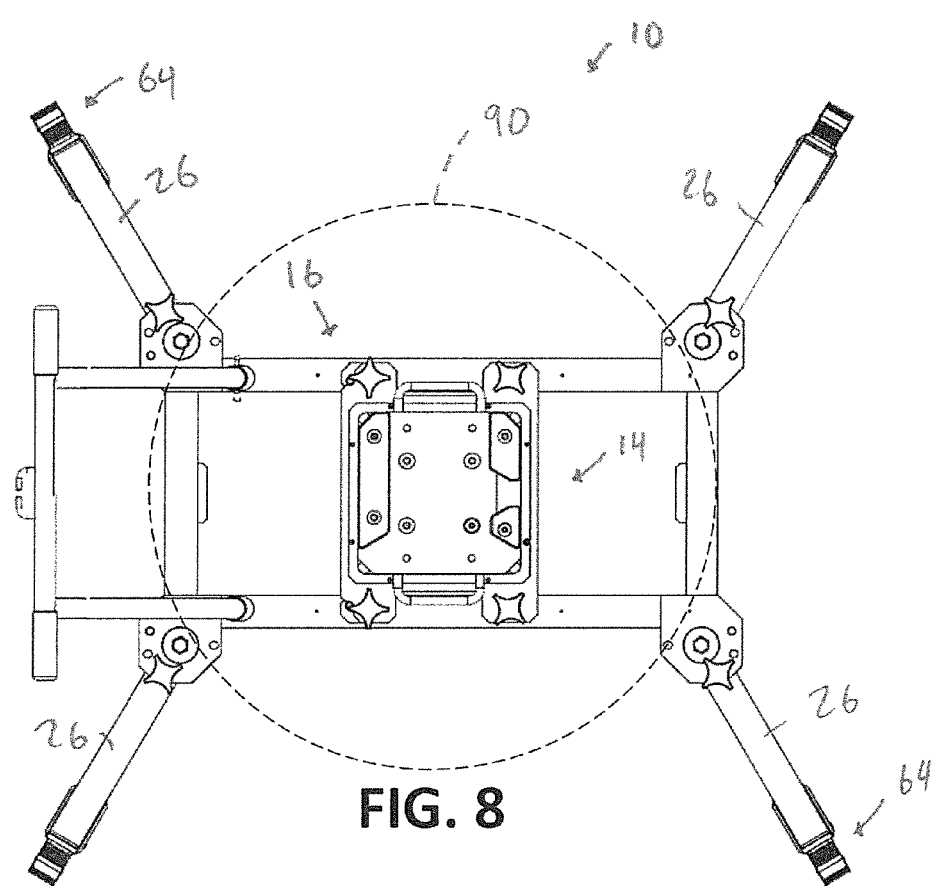
FIG. 8 is a top view of the support apparatus of FIG. 1, in a measurement configuration.

Referring to FIG. 8, when the support assembly 10 is in the vicinity of the LINAC or other treatment device, the legs 26 are moved into the measurement position for maximum stability. The casters 64 are locked in position and further position adjustments can be made using the vertical actuator of the table base assembly 14 and leveling assembly 24. Advantageously, the table base assembly 14 can be located over a bearing floor portion 90 or other local instability without any of the weight of the support assembly 10 being support thereon.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and of the claims appended hereto.

What is claimed is:

1. A support apparatus for a radiotherapy measurement system, the support apparatus comprising:
    a table base assembly having an upper base end and a lower base end, the upper base end being adapted to support a leveling assembly for the radiotherapy measurement system; and;
    a frame assembly to which the lower base end is mounted, the frame assembly having a plurality of frame assembly legs movable to increase and decrease an effective footprint of the frame assembly;
    wherein the frame assembly includes a center frame portion to which the lower end of the table base assembly is mounted and to which the plurality of frame assembly legs are movably connected;
    wherein each of the plurality of frame assembly legs includes a proximal end pivotably connected to the center frame portion and a distal end; and
    wherein each of the plurality of frame assembly legs pivots between a closed position, in which the distal ends are adjacent to the center frame portion and a measurement position, in which the distal ends are pivoted away from the center frame portion to increase the effective footprint.

2. The support apparatus of claim 1, further comprising the leveling assembly for the radiotherapy measurement system mounted to the table base assembly.

3. The support apparatus of claim 1, wherein the lower base end is releasably connected to the frame assembly.

4. The support apparatus of claim 3, wherein the lower base end and the frame assembly are keyed complementarily to prevent releasable connection in an incorrect orientation.

5. The support apparatus of claim 1, wherein the upper base end includes a top plate for releasable connection to the leveling assembly.

6. The support apparatus of claim 5, wherein the top plate is keyed to prevent releasable connection to the leveling assembly in an incorrect orientation.

7. The support apparatus of claim 1, wherein the frame assembly further includes a plurality of locking mechanisms associated with the plurality of frame assembly legs for releasably locking the plurality of frame assembly legs in the closed and measurement positions.

8. The support apparatus of claim 7, wherein each of the locking mechanisms includes a locking pin and a flange attached to the center frame portion having a plurality of holes therein through which the locking pin is insertable, a first of the plurality of holes being aligned with a locking hole in a corresponding one of the plurality of frame assembly legs in the closed position and a second of the plurality of holes being aligned with the locking hole of the corresponding one of the plurality of frame assembly legs in the measurement position.

9. The support apparatus of claim 1, wherein the frame assembly has an effective length and an effective width that are varied by pivoting the plurality of frame assembly legs, both the effective length and width being a minimum in the closed position and greater than the minimum in the measurement position.

10. The support apparatus of claim 9, wherein each of the plurality of frame assembly legs further pivots to a travel position, the effective length being greater and the effective width being lesser in the travel position than in the measurement position.

11. The support apparatus of claim 1, wherein the frame center portion includes a pair of generally opposed first sides connected by a pair of generally opposed second sides, the plurality of frame assembly legs includes two pairs of legs, each pair of legs connected at opposite ends of a respective one of the first sides.

12. The support apparatus of claim 11, wherein, the distal ends of each pair of legs are adjacent to each other along the respective one of the first sides when in the closed position.

13. The support apparatus of claim 12, wherein a primary caster extends downwardly from the distal end of each of the plurality of frame assembly legs.

14. The support apparatus of claim 13, wherein a secondary caster extends downwardly from each of the second sides of the center frame portion.

15. The support apparatus of claim 14, wherein the primary casters extend downwardly further than the secondary casters such that, in the measurement position, the secondary casters will not engage a floor there below.

16. The apparatus of claim 1, wherein the frame assembly further includes a frame handle extending upwardly from the center frame portion.

17. The support apparatus of claim 16, wherein the frame handle is releasably connected to the center frame portion and re-connectable adjacent to the center frame portion in a horizontal orientation.

18. A support apparatus for a radiotherapy measurement system, the support apparatus comprising:
    a table base assembly having an upper base end and a lower base end, the upper base end being adapted to support a leveling assembly for the radiotherapy measurement system; and
    a frame assembly having:
        a center frame portion to which the lower base end is mounted, the center frame portion including a pair of generally opposed first sides connected by a pair of generally opposed second sides;
        first and second pairs of frame assembly legs, each of the frame assembly legs including a proximal end and distal end, each proximal end being pivotably connected to a respective end of one of the first sides such that the first and second pairs of frame assembly legs are pivotable from a closed position, in which their respective distal ends are adjacent to their respective first side and to each other, to a measurement position, in which their respective distal ends are spaced outwardly from their respective first side and apart from each other; and a plurality of primary casters extending downwardly from each of the distal ends.

19. The support apparatus of claim 18, wherein the frame assembly further includes a plurality of locking mechanisms associated with each of the frame assembly legs for releasably locking the frame assembly legs in the closed and measurement positions.

20. The support apparatus of claim 18, wherein the frame assembly further includes a secondary caster extending downwardly from each of the second sides of the center frame portion.

21. The support apparatus of claim 20, wherein each secondary caster extends downwardly less than the primary casters, such that each secondary caster only engages the floor therebelow if the frame assembly tips in the direction thereof in the closed position, and does not engage the floor therebelow in the measurement position.

22. The support apparatus of claim 18, wherein the frame assembly further includes a detachable handle extending upwardly from the center frame portion.

23. The support apparatus of claim 22, wherein the frame assembly further includes attachment brackets for the detachable handle under the center frame portion.

24. The support apparatus of claim 18, wherein the first and second pairs of frame assembly legs are further pivotable to a travel position, in which an overall length of the frame assembly is increased and an overall width of the frame assembly is decreased relative to the measurement position.

\* \* \* \* \*